(12) United States Patent
Fujimura

(10) Patent No.: US 11,169,440 B2
(45) Date of Patent: Nov. 9, 2021

(54) RADIATION-SENSITIVE RESIN COMPOSITION AND ELECTRONIC COMPONENT

(71) Applicant: ZEON CORPORATION, Tokyo (JP)

(72) Inventor: Makoto Fujimura, Tokyo (JP)

(73) Assignee: ZEON CORPORATION, Tokyo (JP)

( * ) Notice: Subject to any disclaimer, the term of this patent is extended or adjusted under 35 U.S.C. 154(b) by 191 days.

(21) Appl. No.: 16/490,694

(22) PCT Filed: Jan. 31, 2018

(86) PCT No.: PCT/JP2018/003203
§ 371 (c)(1),
(2) Date: Sep. 3, 2019

(87) PCT Pub. No.: WO2018/179807
PCT Pub. Date: Oct. 4, 2018

(65) Prior Publication Data
US 2020/0004145 A1    Jan. 2, 2020

(30) Foreign Application Priority Data

Mar. 30, 2017  (JP) .............................. JP2017-068672

(51) Int. Cl.
| | | |
|---|---|---|
| *G03F 7/023* | (2006.01) | |
| *C08F 32/02* | (2006.01) | |
| *C08G 8/10* | (2006.01) | |
| *C08G 59/22* | (2006.01) | |
| *C08K 5/5419* | (2006.01) | |
| *C08L 61/06* | (2006.01) | |
| *G03F 7/075* | (2006.01) | |

(52) U.S. Cl.
CPC ............ *G03F 7/023* (2013.01); *C08F 32/02* (2013.01); *C08G 8/10* (2013.01); *C08G 59/22* (2013.01); *C08K 5/5419* (2013.01); *C08L 61/06* (2013.01); *G03F 7/075* (2013.01); *C08L 2312/08* (2013.01)

(58) Field of Classification Search
CPC ..................................................... G03F 7/004
See application file for complete search history.

(56) References Cited

U.S. PATENT DOCUMENTS

| | | | |
|---|---|---|---|
| 2016/0202607 A1* | 7/2016 | Abe ..................... | G03F 7/0045 |
| | | | 430/280.1 |
| 2017/0017155 A1* | 1/2017 | Tsutsumi .............. | G03F 7/0755 |
| 2017/0023859 A1* | 1/2017 | Tsutsumi ............... | C08G 59/20 |
| 2017/0157969 A1* | 6/2017 | Nakazawa ................. | C09J 7/22 |

FOREIGN PATENT DOCUMENTS

| | | | |
|---|---|---|---|
| JP | 2017181557 A | * 10/2017 | |
| WO | 2010110323 A1 | 9/2010 | |
| WO | 2015141717 A1 | 9/2015 | |
| WO | WO-2015141719 A1 * | 9/2015 | ............... G03F 7/26 |

OTHER PUBLICATIONS

"Table 60 Periodic Table of the Elements", Grant & Hackh's Chemical Dictionary, Fifth Edition, Grant, et al ed, McGraw-Hill Book Company, New York, NY in USPTO, Oct. 23, 1990, pp. 432-433. (Year: 1990).*
Machine Translation of JP2017181557 (Year: 2001).*
Matthias Scholl et al., Synthesis and Activity of a New Generation of Ruthenium-Based Olefin Metathesis Catalysts Coordinated with 1,3-Dimesityl-4,5-dihydroimidazol-2-ylidene Ligands, Organic Letters, 1999, pp. 953-956, vol. 1, No. 6.
Oct. 1, 2018, International Preliminary Report on Patentability issued in the International Patent Application No. PCT/JP2018/003203.

* cited by examiner

*Primary Examiner* — Chanceity N Robinson
(74) *Attorney, Agent, or Firm* — Kenja IP Law PC

(57) ABSTRACT

A radiation-sensitive resin composition capable of forming a resin film for which development residue formation is sufficiently inhibited and that has excellent extensibility. The radiation-sensitive resin composition contains: a cycloolefin polymer (A-1) including a protonic polar group; a cycloolefin polymer (A-2) including a protonic polar group; a difunctional epoxy compound (B); and a radiation-sensitive compound (C). The cycloolefin polymer (A-1) has a weight-average molecular weight of not less than 1,000 and less than 10,000, and the cycloolefin polymer (A-2) has a weight-average molecular weight of not less than 10,000 and not more than 100,000. Content of the cycloolefin polymer (A-2) is not less than 5 mass % and not more than 55 mass % of total content of the cycloolefin polymer (A-1) and the cycloolefin polymer (A-2).

7 Claims, No Drawings

RADIATION-SENSITIVE RESIN COMPOSITION AND ELECTRONIC COMPONENT

TECHNICAL FIELD

The present disclosure relates to a radiation-sensitive resin composition and an electronic component including a resin film obtained using the radiation-sensitive resin composition.

BACKGROUND

Various resin films are included in electronic components such as various display elements, examples of which include organic EL elements and liquid crystal display elements, integrated circuit elements, solid state image sensors, color filters, and black matrices. Examples of such resin films include surface protection films that are provided in order to prevent degradation or damage of an electronic component, planarizing films that are provided for planarizing an element surface or wiring, and interlayer insulating films that are provided in order to insulate between wiring disposed in a layer-like form.

These resin films are conventionally formed, for example, using a radiation-sensitive resin composition that contains a resin component, a crosslinking agent, and a radiation-sensitive compound. Specifically, a resin film having a desired pattern shape in accordance with the intended use thereof can be obtained by irradiating a radiation-sensitive film obtained using a radiation-sensitive resin composition with activating radiation (for example, light such as ultraviolet light (inclusive of ultraviolet light of a single wavelength such as g-line or i-line ultraviolet light), KrF excimer laser light, or ArF excimer laser light; or a particle beam such as an electron beam), removing a photoexposed region of the resultant photoexposed film using a developer to form a developed film, and subsequently crosslinking a resin component in the developed film using a crosslinking agent.

Patent Literature (PTL) 1, for example, reports that through use of a radiation-sensitive resin composition containing a resin component such as a cycloolefin polymer, a specific epoxy crosslinking agent, and a radiation-sensitive compound, solubility of a photoexposed region in developer can be increased, and a resin film having excellent close adherence to metal and low hygroscopicity can be formed.

CITATION LIST

Patent Literature

PTL 1: WO 2015/141717 A1

SUMMARY

Technical Problem

However, with regards to the conventional radiation-sensitive resin composition described above, there has been demand for further increasing the solubility of a photoexposed region in developer so as to further inhibit development residue formation. In the case of the conventional radiation-sensitive resin composition described above, the solubility of a photoexposed region in developer can be increased by lowering the molecular weight of the cycloolefin polymer, for example. However, studies conducted by the inventor have revealed that lowering the molecular weight of the cycloolefin polymer in the conventional radiation-sensitive resin composition described above leads to loss of extensibility of a resin film formed using the radiation-sensitive resin composition. A resin film having poor extensibility in this manner may experience cracking or peeling upon continuous operation of an electronic device including an electronic component or upon impact acting on an electronic component.

Accordingly, an objective of the present disclosure is to provide a radiation-sensitive resin composition capable of forming a resin film for which development residue formation is sufficiently inhibited and that has excellent extensibility, and also to provide an electronic component including a resin film formed using this radiation-sensitive resin composition.

Solution to Problem

The inventor conducted diligent studies with the aim of solving the problems set forth above. As a result, the inventor discovered that through use of a radiation-sensitive resin composition that contains, in a specific quantitative ratio, two types of protonic polar group-containing cycloolefin polymers having weight-average molecular weights within specific ranges as a resin component, and that also contains a difunctional epoxy compound as a crosslinking component, it is possible to sufficiently inhibit development residue formation while also causing a resin film to display excellent extensibility. In this manner, the inventor completed the present disclosure.

Specifically, the present disclosure aims to advantageously solve the problems set forth above by disclosing a radiation-sensitive resin composition comprising: a cycloolefin polymer (A-1) including a protonic polar group; a cycloolefin polymer (A-2) including a protonic polar group; a difunctional epoxy compound (B); and a radiation-sensitive compound (C), wherein the cycloolefin polymer (A-1) has a weight-average molecular weight of not less than 1,000 and less than 10,000 and the cycloolefin polymer (A-2) has a weight-average molecular weight of not less than 10,000 and not more than 100,000, and content of the cycloolefin polymer (A-2) is not less than 5 mass % and not more than 55 mass % of total content of the cycloolefin polymer (A-1) and the cycloolefin polymer (A-2). Through use of the radiation-sensitive resin composition containing the two types of cycloolefin polymers (A-1) and (A-2), differing in terms of weight-average molecular weight, in a specific quantitative ratio, and also containing the difunctional epoxy compound (B) and the radiation-sensitive compound (C) as set forth above, it is possible to sufficiently inhibit development residue formation while also causing a resin film to display excellent extensibility.

Note that "weight-average molecular weight" and "number-average molecular weight" referred to in the present disclosure are values determined as polystyrene-equivalent values by gel permeation chromatography (GPC) using a solvent such as tetrahydrofuran as an eluent.

In the presently disclosed radiation-sensitive resin composition, the difunctional epoxy compound (B) is preferably represented by formula (1), shown below.

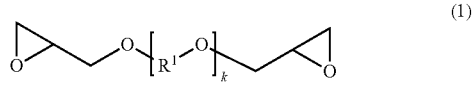

(1)

[In formula (1), $R^1$ is a linear or branched alkylene group having a carbon number of not less than 1 and not more than 15, and k is an integer of not less than 1 and not more than 20.] The use of a difunctional epoxy compound represented by formula (1) can further improve extensibility of a resin film and can reduce the tensile elastic modulus of the resin film to thereby inhibit warping of a substrate including the resin film.

In the presently disclosed radiation-sensitive resin composition, content of the difunctional epoxy compound (B) is preferably 150 parts by mass or more per 100 parts by mass of the cycloolefin polymer (A-2). Extensibility of a resin film can be further improved when the radiation-sensitive resin composition contains 150 parts by mass or more of the difunctional epoxy compound (B) per 100 parts by mass of the cycloolefin polymer (A-2).

The presently disclosed radiation-sensitive resin composition preferably further comprises either or both of a compound including at least two alkoxymethyl groups and a compound including at least two methylol groups. Low hygroscopicity and chemical resistance of a resin film can be improved by using a radiation-sensitive resin composition that contains a compound including at least two alkoxymethyl groups and/or a compound including at least two methylol groups.

Moreover, the presently disclosed radiation-sensitive resin composition preferably further comprises a silane coupling agent. Close adherence of a resin film to metal can be improved by using a radiation-sensitive resin composition that contains a silane coupling agent.

Furthermore, the presently disclosed radiation-sensitive resin composition preferably further comprises an aralkyl phenolic resin. Close adherence of a resin film to metal can be improved by using a radiation-sensitive resin composition that contains an aralkyl phenolic resin.

The present disclosure also aims to advantageously solve the problems set forth above by disclosing an electronic component comprising a resin film formed from any one of the radiation-sensitive resin compositions set forth above. A resin film formed using the radiation-sensitive resin composition set forth above has sufficiently inhibited development residue formation and excellent extensibility, and thus an electronic component including the resin film can sufficiently display desired functions and has high performance.

Advantageous Effect

According to the present disclosure, it is possible to provide a radiation-sensitive resin composition capable of forming a resin film for which development residue formation is sufficiently inhibited and that has excellent extensibility.

Moreover, according to the present disclosure, it is possible to provide an electronic component having high performance.

DETAILED DESCRIPTION

The following provides a detailed description of embodiments of the present disclosure. The presently disclosed radiation-sensitive resin composition can be used in formation of a resin film that can be used as a surface protective film, a planarizing film, an interlayer insulating film, or the like in an electronic component produced by wafer level packaging technology, for example. The presently disclosed electronic component includes a resin film obtained using the presently disclosed radiation-sensitive resin composition.

(Radiation-Sensitive Resin Composition)

The presently disclosed radiation-sensitive resin composition contains a cycloolefin polymer (A) including a protonic polar group, a difunctional epoxy compound (B), and a radiation-sensitive compound (C), and may optionally contain a solvent and other compounding agents. In the presently disclosed radiation-sensitive resin composition, a cycloolefin polymer (A-1) having a weight-average molecular weight of not less than 1,000 and less than 10,000 and a cycloolefin polymer (A-2) having a weight-average molecular weight of not less than 10,000 and not more than 100,000 are contained in a specific quantitative ratio as the cycloolefin polymer (A).

As a result of the presently disclosed radiation-sensitive resin composition containing the two types of cycloolefin polymers (A) set forth above as a resin component and also containing the difunctional epoxy compound (B) as a cross-linking agent, it is possible to ensure solubility of a photo-exposed region of a photoexposed film in developer and sufficiently inhibit development residue formation while also forming a resin film having excellent extensibility when this radiation-sensitive resin composition is used.

<Cycloolefin Polymer (A)>

As previously described, the presently disclosed radiation-sensitive resin composition contains the cycloolefin polymers (A-1) and (A-2), differing in terms of weight-average molecular weight, as the cycloolefin polymer (A) including a protonic polar group.

Note that with regards to descriptions of properties of the "cycloolefin polymer (A)" in the present specification, these should also be considered descriptions of properties that are also relevant to both the "cycloolefin polymer (A-1)" and the "cycloolefin polymer (A-2)" unless otherwise specified.

<<Protonic Polar Group>>

The cycloolefin polymer (A) includes a protonic polar group. As a result of including the protonic polar group, the cycloolefin polymer (A) displays solubility in developer (particularly in alkaline developer described further below) and can be crosslinked by the difunctional epoxy compound (B) to form a desired resin film.

The protonic polar group is a group including an atom belonging to group 15 or group 16 of the periodic table that has a hydrogen atom bonded directly thereto. The atom belonging to group 15 or group 16 of the periodic table is preferably an atom belonging to period 2 or period 3 of group 15 or group 16 of the periodic table, is more preferably an oxygen atom, a nitrogen atom, or a sulfur atom, and is particularly preferably an oxygen atom.

Specific examples of such protonic polar groups include oxygen atom-containing polar groups such as a hydroxy group, a carboxyl group (hydroxycarbonyl group), a sulfo group, and a phosphate group; nitrogen atom-containing polar groups such as a primary amino group, a secondary amino group, a primary amide group, and a secondary amide group (imide group); and sulfur atom-containing polar groups such as a thiol group. Of these protonic polar groups, oxygen atom-containing polar groups are preferable, a carboxyl group and a hydroxy group are more preferable, and a carboxyl group is even more preferable.

It should be noted that the cycloolefin polymer (A) may include just one type of protonic polar group or may include two or more types of protonic polar groups.

<<Chemical Composition>>

No specific limitations are placed on how the protonic polar group described above is introduced into the cycloolefin polymer (A). Specifically, the cycloolefin polymer (A) may be a polymer that includes a repeating unit derived from a cycloolefin monomer (a) including a protonic polar group and that optionally includes repeating units derived from other monomers (b) or may be a polymer obtained by introducing a protonic polar group into a cycloolefin polymer that does not include a protonic polar group using a modifier, for example, and is preferably the former of these polymers.

[Cycloolefin Monomer (a) Including Protonic Polar Group]

No specific limitations are placed on the cycloolefin monomer (a) including a protonic polar group other than being a monomer that includes a cycloolefin structure and any of the protonic polar groups described above. Suitable examples include carboxyl group-containing cycloolefin monomers and hydroxy group-containing cycloolefin monomers.

—Carboxyl Group-Containing Cycloolefin Monomer—

Examples of carboxyl group-containing cycloolefin monomers include 2-hydroxycarbonylbicyclo[2.2.1]hept-5-ene, 2-methyl-2-hydroxycarbonylbicyclo[2.2.1]hept-5-ene, 2-carboxymethyl-2-hydroxycarbonylbicyclo[2.2.1]hept-5-ene, 2-hydroxycarbonyl-2-methoxycarbonylmethylbicyclo[2.2.1]hept-5-ene, 2-hydroxycarbonyl-2-ethoxycarbonylmethylbicyclo[2.2.1]hept-5-ene, 2-hydroxycarbonyl-2-propoxycarbonylmethylbicyclo[2.2.1]hept-5-ene, 2-hydroxycarbonyl-2-butoxycarbonylmethylbicyclo[2.2.1]hept-5-ene, 2-hydroxycarbonyl-2-pentyloxycarbonylmethylbicyclo[2.2.1]hept-5-ene, 2-hydroxycarbonyl-2-hexyloxycarbonylmethylbicyclo[2.2.1]hept-5-ene, 2-hydroxycarbonyl-2-cyclohexyloxycarbonylmethylbicyclo[2.2.1]hept-5-ene, 2-hydroxycarbonyl-2-phenoxycarbonylmethylbicyclo[2.2.1]hept-5-ene, 2-hydroxycarbonyl-2-naphthyloxycarbonylmethylbicyclo[2.2.1]hept-5-ene, 2-hydroxycarbonyl-2-biphenyloxycarbonylmethylbicyclo[2.2.1]hept-5-ene, 2-hydroxycarbonyl-2-benzyloxycarbonylmethylbicyclo[2.2.1]hept-5-ene, 2-hydroxycarbonyl-2-hydroxyethoxycarbonylmethylbicyclo[2.2.1]hept-5-ene, 2,3-dihydroxycarbonylbicyclo[2.2.1]hept-5-ene, 2-hydroxycarbonyl-3-methoxycarbonylbicyclo[2.2.1]hept-5-ene, 2-hydroxycarbonyl-3-ethoxycarbonylbicyclo[2.2.1]hept-5-ene, 2-hydroxycarbonyl-3-propoxycarbonylbicyclo[2.2.1]hept-5-ene, 2-hydroxycarbonyl-3-butoxycarbonylbicyclo[2.2.1]hept-5-ene, 2-hydroxycarbonyl-3-pentyloxycarbonylbicyclo[2.2.1]hept-5-ene, 2-hydroxycarbonyl-3-hexyloxycarbonylbicyclo[2.2.1]hept-5-ene, 2-hydroxycarbonyl-3-cyclohexyloxycarbonylbicyclo[2.2.1]hept-5-ene, 2-hydroxycarbonyl-3-phenoxycarbonylbicyclo[2.2.1]hept-5-ene, 2-hydroxycarbonyl-3-naphthyloxycarbonylbicyclo[2.2.1]hept-5-ene, 2-hydroxycarbonyl-3-biphenyloxycarbonylbicyclo[2.2.1]hept-5-ene, 2-hydroxycarbonyl-3-benzyloxycarbonylbicyclo[2.2.1]hept-5-ene, 2-hydroxycarbonyl-3-hydroxyethoxycarbonylbicyclo[2.2.1]hept-5-ene, 2-hydroxycarbonyl-3-hydroxycarbonylmethylbicyclo[2.2.1]hept-5-ene, 3-methyl-2-hydroxycarbonylbicyclo[2.2.1]hept-5-ene, 3-hydroxymethyl-2-hydroxycarbonylbicyclo[2.2.1]hept-5-ene, 2-hydroxycarbonyltricyclo[5.2.1.0$^{2,6}$]deca-3,8-diene, 4-hydroxycarbonyltetracyclo[6.2.1.1$^{3,6}$.0$^{2,7}$]dodec-9-ene, 4-methyl-4-hydroxycarbonyltetracyclo[6.2.1.1$^{3,6}$.0$^{2,7}$]dodec-9-ene, 4,5-dihydroxycarbonyltetracyclo[6.2.1.1$^{3,6}$.0$^{2,7}$]dodec-9-ene, 4-carboxymethyl-4-hydroxycarbonyltetracyclo[6.2.1.1$^{3,6}$.0$^{2,7}$]dodec-9-ene, N-(hydroxycarbonylmethyl)bicyclo[2.2.1]hept-5-ene-2,3-dicarboxyimide, N-(hydroxycarbonylethyl)bicyclo[2.2.1]hept-5-ene-2,3-dicarboxyimide, N-(hydroxycarbonylpentyl)bicyclo[2.2.1]hept-5-ene-2,3-dicarboxyimide, N-(dihydroxycarbonylethyl)bicyclo[2.2.1]hept-5-ene-2,3-dicarboxyimide, N-(dihydroxycarbonylpropyl)bicyclo[2.2.1]hept-5-ene-2,3-dicarboxyimide, N-(hydroxycarbonylphenethyl)bicyclo[2.2.1]hept-5-ene-2,3-dicarboxyimide, N-(2-(4-hydroxyphenyl)-1-(hydroxycarbonyl)ethyl)bicyclo[2.2.1]hept-5-ene-2,3-dicarboxyimide, and N-(hydroxycarbonylphenyl)bicyclo[2.2.1]hept-5-ene-2,3-dicarboxyimide.

—Hydroxy Group-Containing Cycloolefin Monomer—

Examples of hydroxy group-containing cycloolefin monomers include 2-(4-hydroxyphenyl)bicyclo[2.2.1]hept-5-ene, 2-methyl-2-(hydroxyphenyl)bicyclo[2.2.1]hept-5-ene, 4-(4-hydroxyphenyl)tetracyclo[6.2.1.1$^{3,6}$.0$^{2,7}$]dodec-9-ene, 4-methyl-4-(4-hydroxyphenyl)tetracyclo[6.2.1.1$^{3,6}$.0$^{2,7}$]dodec-9-ene, 2-hydroxybicyclo[2.2.1]hept-5-ene, 2-hydroxymethylbicyclo[2.2.1]hept-5-ene, 2-hydroxyethylbicyclo[2.2.1]hept-5-ene, 2-methyl-2-hydroxymethylbicyclo[2.2.1]hept-5-ene, 2,3-dihydroxymethylbicyclo[2.2.1]hept-5-ene, 2-(hydroxyethoxycarbonyl)bicyclo[2.2.1]hept-5-ene, 2-methyl-2-(hydroxyethoxycarbonyl)bicyclo[2.2.1]hept-5-ene, 2-(1-hydroxy-1-trifluoromethyl-2,2,2-trifluoroethyl)bicyclo[2.2.1]hept-5-ene, 2-(2-hydroxy-2-trifluoromethyl-3,3,3-trifluoropropyl)bicyclo[2.2.1]hept-5-ene, 3-hydroxytricyclo[5.2.1.0$^{2,6}$]deca-4,8-diene, 3-hydroxymethyltricyclo[5.2.1.0$^{2,6}$]deca-4,8-diene, 4-hydroxytetracyclo[6.2.1.1$^{3,6}$.0$^{2,7}$]dodec-9-ene, 4-hydroxymethyltetracyclo[6.2.1.1$^{3,6}$.0$^{2,7}$]dodec-9-ene, 4,5-dihydroxymethyltetracyclo[6.2.1.1$^{3,6}$.0$^{2,7}$]dodec-9-ene, 4-(hydroxyethoxycarbonyl)tetracyclo[6.2.1.1$^{3,6}$.0$^{2,7}$]dodec-9-ene, 4-methyl-4-(hydroxyethoxycarbonyl)tetracyclo[6.2.1.1$^{3,6}$.0$^{2,7}$]dodec-9-ene, N-(hydroxyethyl)bicyclo[2.2.1]hept-5-ene-2,3-dicarboxyimide, and N-(hydroxyphenyl)bicyclo[2.2.1]hept-5-ene-2,3-dicarboxyimide.

Of these cycloolefin monomers, carboxyl group-containing cycloolefin monomers are preferable, and 4-hydroxycarbonyltetracyclo[6.2.1.1$^{3,6}$.0$^{2,7}$]dodec-9-ene is more preferable from a viewpoint of increasing solubility in developer (particularly alkaline developer described further below) and improving close adherence of a resin film to metal. The cycloolefin monomer (a) may be one type of monomer used individually or two or more types of monomers used in combination.

—Percentage Content—

The percentage content of the repeating unit derived from the cycloolefin monomer (a) in the cycloolefin polymer (A) when all repeating units are taken to be 100 mol % is preferably 10 mol % or more, more preferably 20 mol % or more, and even more preferably 30 mol % or more, and is preferably 90 mol % or less, more preferably 80 mol % or less, and even more preferably 70 mol % or less. Development residue formation can be further inhibited when the proportion constituted by the repeating unit derived from the cycloolefin monomer (a) is 10 mol % or more, whereas sufficient solubility of the cycloolefin polymer (A) in solvent can be ensured when the proportion constituted by the repeating unit derived from the cycloolefin monomer (a) is 90 mol % or less.

[Other Monomers (b)]

No specific limitations are placed on other monomers (b) that may be used other than being monomers that are copolymerizable with the cycloolefin monomer (a) described above. Examples of monomers that are copolymerizable with the cycloolefin monomer (a) include a cycloolefin monomer (b1) including a polar group other than a protonic polar group, a cycloolefin monomer (b2) not including a polar group, and a monomer (b3) other than a cycloolefin monomer.

—Monomer (b1)—

The cycloolefin monomer (b1) including a polar group other than a protonic polar group may, for example, be a cycloolefin monomer that includes an N-substituted imide group, an ester group, a cyano group, an acid anhydride group, or a halogen atom.

Examples of N-substituted imide group-containing cycloolefin monomers include monomers represented by the following formula (2) and monomers represented by the following formula (3).

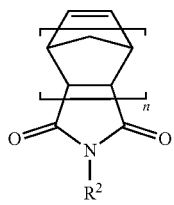

(2)

[In formula (2), $R^2$ represents an alkyl group having a carbon number of not less than 1 and not more than 16 or an aryl group, and n represents 1 or 2.]

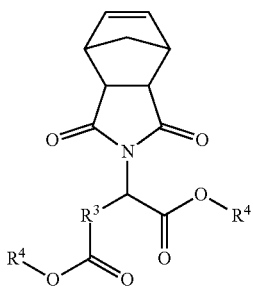

(3)

[In formula (3), $R^3$ represents a divalent alkylene group having a carbon number of not less than 1 and not more than 3, and $R^4$ represents a monovalent alkyl group having a carbon number of not less than 1 and not more than 10 or a monovalent haloalkyl group having a carbon number of not less than 1 and not more than 10. Note that the two $R^4$ groups may be the same or different.]

Examples of alkyl groups having a carbon number of not less than 1 and not more than 16 that may be represented by $R^2$ in formula (2) include linear alkyl groups such as a methyl group, an ethyl group, an n-propyl group, an n-butyl group, an n-pentyl group, an n-hexyl group, an n-heptyl group, an n-octyl group, an n-nonyl group, an n-decyl group, an n-undecyl group, an n-dodecyl group, an n-tridecyl group, an n-tetradecyl group, an n-pentadecyl group, and an n-hexadecyl group; cyclic alkyl groups such as a cyclopropyl group, a cyclobutyl group, a cyclopentyl group, a cyclohexyl group, a cycloheptyl group, a cyclooctyl group, a cyclononyl group, a cyclodecyl group, a cycloundecyl group, a cyclododecyl group, a norbornyl group, a bornyl group, an isobornyl group, a decahydronaphthyl group, a tricyclodecanyl group, and an adamantyl group; and branched alkyl groups such as a 2-propyl group, a 2-butyl group, a 2-methyl-1-propyl group, a 2-methyl-2-propyl group, a 1-methylbutyl group, a 2-methylbutyl group, a 1-methylpentyl group, a 1-ethylbutyl group, a 2-methylhexyl group, a 2-ethylhexyl group, a 4-methylheptyl group, a 1-methylnonyl group, a 1-methyltridecyl group, and a 1-methyltetradecyl group.

Examples of aryl groups that may be represented by $R^2$ in formula (2) include a benzyl group.

Of these examples, alkyl groups having a carbon number of not less than 4 and not more than 14 and aryl groups are preferable, and alkyl groups having a carbon number of not less than 6 and not more than 10 and aryl groups are more preferable from a viewpoint of improving solubility of the cycloolefin polymer (A) in solvent and ensuring sufficient heat resistance of a resin film in order to inhibit pattern loss by melting due to heat during patterning.

Specific examples of monomers represented by formula (2) include bicyclo[2.2.1]hept-5-ene-2,3-dicarboxyimide, N-phenyl-bicyclo[2.2.1]hept-5-ene-2,3-dicarboxyimide, N-methylbicyclo[2.2.1]hept-5-ene-2,3-dicarboxyimide, N-ethylbicyclo[2.2.1]hept-5-ene-2,3-dicarboxyimide, N-propylbicyclo[2.2.1]hept-5-ene-2,3-dicarboxyimide, N-butylbicyclo[2.2.1]hept-5-ene-2,3-dicarboxyimide, N-cyclohexylbicyclo[2.2.1]hept-5-ene-2,3-dicarboxyimide, N-adamantylbicyclo[2.2.1]hept-5-ene-2,3-dicarboxyimide, N-(1-methylbutyl)-bicyclo[2.2.1]hept-5-ene-2,3-dicarboxyimide, N-(2-methylbutyl)-bicyclo[2.2.1]hept-5-ene-2,3-dicarboxyimide, N-(1-methylpentyl)-bicyclo[2.2.1]hept-5-ene-2,3-dicarboxyimide, N-(2-methylpentyl)-bicyclo[2.2.1]hept-5-ene-2,3-dicarboxyimide, N-(1-ethylbutyl)-bicyclo[2.2.1]hept-5-ene-2,3-dicarboxyimide, N-(2-ethylbutyl)-bicyclo[2.2.1]hept-5-ene-2,3-dicarboxyimide, N-(1-methylhexyl)-bicyclo[2.2.1]hept-5-ene-2,3-dicarboxyimide, N-(2-methylhexyl)-bicyclo[2.2.1]hept-5-ene-2,3-dicarboxyimide, N-(3-methylhexyl)-bicyclo[2.2.1]hept-5-ene-2,3-dicarboxyimide, N-(1-butylpentyl)-bicyclo[2.2.1]hept-5-ene-2,3-dicarboxyimide, N-(2-butylpentyl)-bicyclo[2.2.1]hept-5-ene-2,3-dicarboxyimide, N-(1-methylheptyl)-bicyclo[2.2.1]hept-5-ene-2,3-dicarboxyimide, N-(2-methylheptyl)-bicyclo[2.2.1]hept-5-ene-2,3-dicarboxyimide, N-(3-methylheptyl)-bicyclo[2.2.1]hept-5-ene-2,3-dicarboxyimide, N-(4-methylheptyl)-bicyclo[2.2.1]hept-5-ene-2,3-dicarboxyimide, N-(1-ethylhexyl)-bicyclo[2.2.1]hept-5-ene-2,3-dicarboxyimide, N-(2-ethylhexyl)-bicyclo[2.2.1]hept-5-ene-2,3-dicarboxyimide, N-(3-ethylhexyl)-bicyclo[2.2.1]hept-5-ene-2,3-dicarboxyimide, N-(1-propylpentyl)-bicyclo[2.2.1]hept-5-ene-2,3-dicarboxyimide, N-(2-propylpentyl)-bicyclo[2.2.1]hept-5-ene-2,3-dicarboxyimide, N-(1-methyloctyl)-bicyclo[2.2.1]hept-5-ene-2,3-dicarboxyimide, N-(2-methyloctyl)-bicyclo[2.2.1]hept-5-ene-2,3-dicarboxyimide, N-(3-methyloctyl)-bicyclo[2.2.1]hept-5-ene-2,3-dicarboxyimide, N-(4-methyl octyl)-bicyclo[2.2.1]hept-5-ene-2,3-dicarboxyimide, N-(1-ethylheptyl)-bicyclo[2.2.1]hept-5-ene-2,3-dicarboxyimide, N-(2-ethylheptyl)-bicyclo[2.2.1]hept-5-ene-2,3-dicarboxyimide, N-(3-ethylheptyl)-bicyclo[2.2.1]hept-5-ene-2,3-dicarboxyimide, N-(4-ethylheptyl)-bicyclo[2.2.1]hept-5-ene-2,3-dicarboxyimide, N-(1-propylhexyl)-bicyclo[2.2.1]hept-5-ene-2,3-dicarboxyimide, N-(2-propylhexyl)-bicyclo[2.2.1]hept-5-ene-2,3-dicarboxyimide, N-(3-propylhexyl)-bicyclo[2.2.1]hept-5-ene-2,3-dicarboxyimide, N-(1-methylnonyl)-bicyclo[2.2.1]hept-5-ene-2,3-dicarboxyimide, N-(2-methylnonyl)-bicyclo[2.2.1]hept-5-ene-2,3-dicarboxyimide, N-(3-methylnonyl)-bicyclo[2.2.1]hept-5-ene-2,3-dicarboxyimide, N-(4-methylnonyl)-bicyclo[2.2.1]hept-5-ene-2,3-dicarboxyimide, N-(5-methylnonyl)- bicyclo[2.2.1]hept-5-ene-2,3-dicarboxyimide, N-(1-ethyloctyl)-bicyclo[2.2.1]hept-5-ene-2,3-dicarboxyimide, N-(2-ethyloctyl)-bicyclo[2.2.1]hept-5-ene-2,3-dicarboxyimide, N-(3-ethyloctyl)-bicyclo[2.2.1]hept-5-ene-2,3-dicarboxyimide, N-(4-ethyloctyl)-bicyclo[2.2.1]hept-5-ene-2,3-dicarboxyimide, N-(1-methyldecyl)-bicyclo[2.2.1]hept-5-ene-2,3-dicarboxyimide, N-(1-methyldodecyl)-bicyclo[2.2.1]hept-5-ene-2,3-dicarboxyimide, N-(1-methylundecyl)-bicyclo[2.2.1]hept-5-ene-2,3-dicarboxyimide, N-(1-methyldodecyl)-bicyclo[2.2.1]hept-5-ene-2,3-dicarboxyimide, N-(1-methyltridecyl)-bicyclo[2.2.1]hept-5-ene-2,3-dicarboxyimide, N-(1-methyltetradecyl)-bicyclo[2.2.1]hept-5-ene-2,3-dicarboxyimide, N-(1-methylpentadecyl)-bicyclo[2.2.1]hept-5-ene-2,3-dicarboxyimide, N-phenyl-tetracyclo[6.2.1.1$^{3,6}$.0$^{2,7}$]dodec-9-ene-4,5-dicarboxyimide, and N-(2,4-dimethoxyphenyl)-tetracyclo[6.2.1.1$^{3,6}$.0$^{2,7}$]dodec-9-ene-4,5-dicarboxy imide.

Examples of divalent alkylene groups having a carbon number of not less than 1 and not more than 3 that may be represented by $R^3$ in formula (3) include a methylene group, an ethylene group, a propylene group, and an isopropylene group. Of these alkylene groups, a methylene group and an ethylene group are preferable because they provide good polymerization activity.

Examples of monovalent alkyl groups having a carbon number of not less than 1 and not more than 10 that may be represented by $R^4$ in formula (3) include a methyl group, an ethyl group, a propyl group, an isopropyl group, a butyl group, a sec-butyl group, a tert-butyl group, a hexyl group, and a cyclohexyl group.

Examples of monovalent haloalkyl groups having a carbon number of not less than 1 and not more than 10 that may be represented by $R^4$ in formula (3) include a fluoromethyl group, a chloromethyl group, a bromomethyl group, a difluoromethyl group, a dichloromethyl group, a difluoromethyl group, a trifluoromethyl group, a trichloromethyl group, a 2,2,2-trifluoroethyl group, a pentafluoroethyl group, a heptafluoropropyl group, a perfluorobutyl group, and a perfluoropentyl group.

Of these examples, a methyl group and an ethyl group are preferable as $R^4$ from a viewpoint of improving solubility of the cycloolefin polymer (A) in solvent.

The monomers represented by formulae (2) and (3) can be obtained, for example, through an imidization reaction of a corresponding amine and 5-norbornene-2,3-dicarboxylic anhydride. Moreover, the obtained monomer can be efficiently isolated by using a commonly known method to perform separation and purification of the reaction liquid obtained through the imidization reaction.

Examples of ester group-containing cycloolefin monomers include 2-acetoxybicyclo[2.2.1]hept-5-ene, 2-acetoxymethylbicyclo[2.2.1]hept-5-ene, 2-methoxycarbonylbicyclo[2.2.1]hept-5-ene, 2-ethoxycarbonylbicyclo[2.2.1]hept-5-ene, 2-propoxycarbonylbicyclo[2.2.1]hept-5-ene, 2-butoxycarbonylbicyclo[2.2.1]hept-5-ene, 2-cyclohexyloxycarbonylbicyclo[2.2.1]hept-5-ene, 2-methyl-2-methoxycarbonylbicyclo[2.2.1]hept-5-ene, 2-methyl-2-ethoxycarbonylbicyclo[2.2.1]hept-5-ene, 2-methyl-2-propoxycarbonylbicyclo[2.2.1]hept-5-ene, 2-methyl-2-butoxycarbonylbicyclo[2.2.1]hept-5-ene, 2-methyl-2-cyclohexyloxycarbonylbicyclo[2.2.1]hept-5-ene, 2-(2,2,2-trifluoroethoxycarbonyl)bicyclo[2.2.1]hept-5-ene, 2-methyl-2-(2,2,2-trifluoroethoxycarbonyl)bicyclo[2.2.1]hept-5-ene, 2-methoxycarbonyltricyclo[5.2.1.0$^{2,6}$]dec-8-ene, 2-ethoxycarbonyltricyclo[5.2.1.0$^{2,6}$]dec-8-ene, 2-propoxycarbonyltricyclo[5.2.1.0$^{2,6}$]dec-8-ene, 4-acetoxytetracyclo[6.2.1.1$^{3,6}$.0$^{2,7}$]dodec-9-ene, 4-methoxycarbonyltetracyclo[6.2.1.1$^{3,6}$.0$^{2,7}$]dodec-9-ene, 4-ethoxycarbonyltetracyclo[6.2.1.1$^{3,6}$.0$^{2,7}$]dodec-9-ene, 4-propoxycarbonyltetracyclo[6.2.1.1$^{3,6}$.0$^{2,7}$]dodec-9-ene, 4-butoxycarbonyltetracyclo[6.2.1.1$^{3,6}$.0$^{2,7}$]dodec-9-ene, 4-methyl-4-methoxycarbonyltetracyclo[6.2.1.1$^{3,6}$.0$^{2,7}$]dodec-9-ene, 4-methyl-4-ethoxycarbonyltetracyclo[6.2.1.1$^{3,6}$.0$^{2,7}$]dodec-9-ene, 4-methyl-4-propoxycarbonyltetracyclo[6.2.1.1$^{3,6}$.0$^{2,7}$]dodec-9-ene, 4-methyl-4-butoxycarbonyltetracyclo[6.2.1.1$^{3,6}$.0$^{2,7}$]dodec-9-ene, 4-(2,2,2-trifluoroethoxycarbonyl)tetracyclo[6.2.1.1$^{3,6}$.0$^{2,7}$]dodec-9-ene, and 4-methyl-4-(2,2,2-trifluoroethoxycarbonyl)tetracyclo[6.2.1.1$^{3,6}$.0$^{2,7}$]dodec-9-ene.

Examples of cyano group-containing cycloolefin monomers include 4-cyanotetracyclo[6.2.1.1$^{3,6}$.0$^{2,7}$]dodec-9-ene, 4-methyl-4-cyanotetracyclo[6.2.1.1$^{3,6}$.0$^{2,7}$]dodec-9-ene, 4,5-dicyanotetracyclo[6.2.1.1$^{3,6}$.0$^{2,7}$]dodec-9-ene, 2-cyanobicyclo[2.2.1]hept-5-ene, 2-methyl-2-cyanobicyclo[2.2.1]hept-5-ene, and 2,3-dicyanobicyclo[2.2.1]hept-5-ene.

Examples of acid anhydride group-containing cycloolefin monomers include tetracyclo[6.2.1.1$^{3,6}$.0$^{2,7}$]dodec-9-ene-4,5-dicarboxylic anhydride, bicyclo[2.2.1]hept-5-ene-2,3-dicarboxylic anhydride, and 2-carboxymethyl-2-hydroxycarbonylbicyclo[2.2.1]hept-5-ene anhydride.

Examples of halogen atom-containing cycloolefin monomers include 2-chlorobicyclo[2.2.1]hept-5-ene, 2-chloromethylbicyclo[2.2.1]hept-5-ene, 2-(chlorophenyl)bicyclo[2.2.1]hept-5-ene, 4-chlorotetracyclo[6.2.1.1$^{3,6}$.0$^{2,7}$]dodec-9-ene, and 4-methyl-4-chlorotetracyclo[6.2.1.1$^{3,6}$.0$^{2,7}$]dodec-9-ene.

—Monomer (b2)—

Examples of the cycloolefin monomer (b2) that does not include a polar group include bicyclo[2.2.1]hept-2-ene (also referred to as "norbornene"), 5-ethyl-bicyclo[2.2.1]hept-2-ene, 5-butyl-bicyclo[2.2.1]hept-2-ene, 5-ethylidene-bicyclo[2.2.1]hept-2-ene, 5-methylidene-bicyclo[2.2.1]hept-2-ene, 5-vinyl-bicyclo[2.2.1]hept-2-ene, tricyclo[5.2.1.0$^{2,6}$]deca-3,8-diene (common name: dicyclopentadiene), tetracyclo[10.2.1.0$^{2,11}$.0$^{4,9}$]pentadeca-4,6,8,13-tetraene, tetracyclo[6.2.1.1$^{3,6}$.0$^{2,7}$]dodec-4-ene (also referred to as "tetracyclododecene"), 9-methyl-tetracyclo[6.2.1.1$^{3,6}$.0$^{2,7}$]dodec-4-ene, 9-ethyl-tetracyclo[6.2.1.1$^{3,6}$.0$^{2,7}$]dodec-4-ene, 9-methylidene-tetracyclo[6.2.1.1$^{3,6}$.0$^{2,7}$]dodec-4-ene, 9-ethylidene-tetracyclo[6.2.1.1$^{3,6}$.0$^{2,7}$]dodec-4-ene, 9-vinyl-tetracyclo[6.2.1.1$^{3,6}$.0$^{2,7}$]dodec-4-ene, 9-propenyl-tetracyclo[6.2.1.1$^{3,6}$.0$^{2,7}$]dodec-4-ene, pentacyclo[9.2.1.1$^{3,9}$.0$^{2,10}$.0$^{4,8}$]pentadeca-5,12-diene, cyclobutene, cyclopentene, cyclopentadiene, cyclohexene, cycloheptene, cyclooctene, cyclooctadiene, indene, 3a,5,6,7a-tetrahydro-4,7-methano-1H-indene, 9-phenyl-tetracyclo[6.2.1.1$^{3,6}$.0$^{2,7}$]dodec-4-ene, tetracyclo[9.2.1.0$^{2,10}$.0$^{3,8}$]tetradeca-3,5,7,12-tetraene, and pentacyclo[9.2.1.1$^{3,9}$.0$^{2,10}$.0$^{4,8}$]pentadec-12-ene.

—Monomer (b3)—

Examples of the monomer (b3) other than a cycloolefin include ethylene; α-olefins having a carbon number of not less than 3 and not more than 20 such as propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene, and 1-eicosene; and non-conjugated dienes such as 1,4-hexadiene, 1,5-hexadiene, 4-methyl-1,4-hexadiene, 5-methyl-1,4-hexadiene, and 1,7-octadiene, and derivatives thereof.

The other monomers (b), such as the monomers (b1) to (b3) described above, may be one type of monomer used individually or two or more types of monomers used in combination. Of these monomers, a cycloolefin monomer (b1) including a polar group other than a protonic polar group is preferable, and an N-substituted imide group-containing cycloolefin monomer is more preferable from a viewpoint of improving heat resistance of a resin film.

—Percentage Content—

The percentage content of repeating units derived from other monomers (b) in the cycloolefin polymer (A) when all repeating units are taken to be 100 mol % is preferably 10 mol % or more, more preferably 20 mol % or more, and even more preferably 30 mol % or more, and is preferably 90 mol % or less, more preferably 80 mol % or less, and even more preferably 70 mol % or less. Sufficient solubility of the cycloolefin polymer (A) in solvent can be ensured when the proportion constituted by repeating units derived from other monomers (b) is 10 mol % or more, whereas development residue formation can be further inhibited when the proportion constituted by repeating units derived from other monomers (b) is 90 mol % or less.

<<Preparation Method of Cycloolefin Polymer (A)>>

Examples of methods by which the cycloolefin polymer (A) including a protonic polar group may be prepared include, but are not specifically limited to, methods (i) and (ii) described below.

(i) A method in which a monomer composition containing a cycloolefin monomer (a) including a protonic polar group and other optionally used monomers (b) is polymerized and then a hydrogenation reaction is optionally carried out (ii) A method in which a cycloolefin polymer that does not include a protonic polar group is modified using a modifier including a protonic polar group Of these methods, method (i) is preferable.

[Preparation Method (i)]

The method of polymerization of the monomer composition containing a cycloolefin monomer (a) and optionally containing other monomers (b) may be any known method without any specific limitations. Specifically, the polymerization method may be ring-opening polymerization or addition polymerization, for example, and is preferably ring-opening polymerization. In other words, the cycloolefin polymer (A) is preferably a ring-opened polymer or an addition polymer, and is more preferably a ring-opened polymer.

The method of ring-opening polymerization may, for example, be a method in which ring-opening metathesis polymerization of a cycloolefin monomer (a) including a protonic polar group and other monomers (b) used as necessary is carried out in the presence of a metathesis reaction catalyst. A method described in WO 2010/110323 A1, for example, may be adopted as the method of ring-opening metathesis polymerization.

In a case in which ring-opening polymerization is used in preparation of the cycloolefin polymer (A), it is preferable that the obtained ring-opened polymer is subjected to a hydrogenation reaction to yield a hydrogenated product in which carbon-carbon double bonds included in the main chain of the polymer have been hydrogenated. The proportion of carbon-carbon double bonds that are hydrogenated (percentage hydrogenation) in a case in which the cycloolefin polymer (A) is a hydrogenated product is preferably 50% or more, more preferably 70% or more, even more preferably 90% or more, and particularly preferably 95% or more from a viewpoint of improving heat resistance of a resin film.

The "percentage hydrogenation" referred to in the present disclosure can be measured using a $^1$H-NMR spectrum.

[Preparation Method (ii)]

No specific limitations are placed on how a cycloolefin polymer that does not include a protonic polar group is prepared. For example, a cycloolefin polymer that does not include a protonic polar group can be obtained by optionally combining at least one of the previously described monomers (b1) and (b2) with a monomer (b3) as necessary and performing polymerization thereof by a known method. Modification of the obtained polymer with a modifier including a protonic polar group can be carried out by a standard method and is normally performed in the presence of a radical generator.

Note that a compound that includes both a protonic polar group and a reactive carbon-carbon unsaturated bond may be used as the modifier including a protonic polar group. Specifically, a compound such as described in WO 2015/141717 A1 may be used.

<<Weight-Average Molecular Weight of Cycloolefin Polymers (A-1) and (A-2)>>

As previously described, the cycloolefin polymers (A-1) and (A-2) that differ in terms of weight-average molecular weight are used together in a specific quantitative ratio in the presently disclosed radiation-sensitive resin composition. As a result of the cycloolefin polymer (A-1) having a comparatively low molecular weight and the cycloolefin polymer (A-2) having a comparatively high molecular weight being used together in the specific quantitative ratio described further below, extensibility of a resin film can be improved and development residue formation can be sufficiently inhibited compared to in cases in which these cycloolefin polymers are used individually. Although it is not clear why extensibility of a resin film is improved through combined use of the cycloolefin polymers (A-1) and (A-2) in a specific quantitative ratio, the reason for this is presumed to be that crosslinking performed with high molecular weight and low molecular weight cycloolefin polymers mixed in a specific quantitative ratio results in formation of a crosslinked structure in which tangling of molecule chains is not easily undone upon extension.

The weight-average molecular weight of the cycloolefin polymer (A-1) is required to be not less than 1,000 and less than 10,000, is preferably 2,000 or more, more preferably 3,000 or more, even more preferably 4,000 or more, and particularly preferably 5,000 or more, and is preferably 9,000 or less, and more preferably 8,000 or less. Extensibility of a resin film cannot be ensured if the weight-average molecular weight of the cycloolefin polymer (A-1) is less than 1,000, whereas development residue formation cannot be sufficiently inhibited if the weight-average molecular weight of the cycloolefin polymer (A-1) is 10,000 or more.

The weight-average molecular weight of the cycloolefin polymer (A-2) is required to be not less than 10,000 and not more than 100,000, is preferably 13,000 or more, more preferably 15,000 or more, and even more preferably 18,000 or more, and is preferably 95,000 or less, more preferably 90,000 or less, even more preferably 70,000 or less, and particularly preferably 50,000 or less. Extensibility of a resin film cannot be ensured if the weight-average molecular weight of the cycloolefin polymer (A-2) is less than 10,000, whereas development residue formation cannot be sufficiently inhibited if the weight-average molecular weight of the cycloolefin polymer (A-2) is more than 100,000.

The weight-average molecular weight of the cycloolefin polymer (A) can be controlled to within a desired range by adjusting the synthesis conditions (for example, the amount of molecular weight modifier).

<<Molecular Weight Distribution of Cycloolefin Polymers (A-1) and (A-2)>>

The molecular weight distribution (weight-average molecular weight/number-average molecular weight) of each of the cycloolefin polymers (A-1) and (A-2) is preferably 4 or less, more preferably 3 or less, and even more preferably 2.5 or less. When the molecular weight distribution of each of the cycloolefin polymers (A-1) and (A-2) is 4 or less, the effect of combined use of two types of cycloolefin polymers (A) differing in terms of weight-average molecular weight can be sufficiently displayed, development residue formation can be sufficiently inhibited, and extensibility of a resin film can be further improved.

Note that the molecular weight distribution of the cycloolefin polymer (A) can be reduced by a method described in JP 2006-307155 A, for example.

<<Content Ratio of Cycloolefin Polymers (A-1) and (A-2)>>

The content of the cycloolefin polymer (A-2) is required to be not less than 5 mass % and not more than 55 mass % of the total content of the cycloolefin polymer (A-1) and the cycloolefin polymer (A-2), is preferably 7 mass % or more, more preferably 10 mass % or more, even more preferably 12 mass % or more, and particularly preferably 15 mass % or more of the total content of the cycloolefin polymer (A-1) and the cycloolefin polymer (A-2), and is preferably 45 mass % or less, more preferably 40 mass % or less, and even more preferably 35 mass % or less of the total content of the cycloolefin polymer (A-1) and the cycloolefin polymer (A-2). Extensibility of a resin film cannot be ensured if the proportion constituted by content of the cycloolefin polymer (A-2) among the total content of the cycloolefin polymers (A-1) and (A-2) is less than 5 mass %, whereas development residue formation cannot be sufficiently inhibited and extensibility of a resin film decreases if this proportion is more than 55 mass %.

<Difunctional Epoxy Compound (B)>

The difunctional epoxy compound (B) is a compound including two epoxy groups per molecule. The difunctional epoxy compound (B) acts as a crosslinking agent for crosslinking the cycloolefin polymer (A) in the presently disclosed radiation-sensitive resin composition. As a result of the difunctional epoxy compound (B) being used as a crosslinking agent, the cycloolefin polymer (A) can retain a relatively high degree of freedom in an obtained crosslinked structure compared to a case in which, for example, only an epoxy compound having a functionality of 3 or more is used as a crosslinking agent. Consequently, the use of the difunctional epoxy compound (B) as a crosslinking agent can contribute to improving extensibility of an obtained resin film.

The difunctional epoxy compound (B) may be one type of compound used individually or two or more types of compounds used in combination.

<<Suitable Difunctional Epoxy Compound (B)>>

The difunctional epoxy compound (B) is preferably a difunctional epoxy compound represented by the following formula (1) from a viewpoint of further improving extensibility of a resin film and reducing the tensile elastic modulus of the resin film to inhibit warping of a substrate including the resin film, but is not specifically limited thereto.

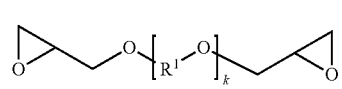

In formula (1), $R^1$ is a linear or branched alkylene group having a carbon number of not less than 1 and not more than 15, is preferably a linear or branched alkylene group having a carbon number of not less than 2 and not more than 10, and is more preferably a linear or branched alkylene group having a carbon number of not less than 3 and not more than 8. Moreover, $R^1$ is preferably a linear alkylene group from a viewpoint of further improving extensibility of a resin film while also further reducing the tensile elastic modulus of the resin film. Furthermore, k in formula (1) is an integer of not less than 1 and not more than 20, is preferably an integer of not less than 1 and not more than 18, and is more preferably an integer of not less than 2 and not more than 15.

<<Properties>>

The epoxy equivalent of the difunctional epoxy compound (B) is preferably not less than 100 and not more than 1,000, more preferably not less than 200 and not more than 800, and even more preferably not less than 300 and not more than 600 from a viewpoint of further improving extensibility of a resin film while also further reducing the tensile elastic modulus of the resin film. The "epoxy equivalent" can be measured in accordance with JIS K 7236 "Determination of epoxy equivalent in epoxy resins", for example.

The softening point of the difunctional epoxy compound (B) is preferably 40° C. or lower, and more preferably 25° C. or lower from a viewpoint of further improving extensibility of a resin film while also further reducing the tensile elastic modulus of the resin film. In other words, the difunctional epoxy compound (B) is preferably a liquid at normal temperature (25° C.). The "softening point" can be measured in accordance with JIS K 2207, for example.

<<Content>>

The content of the difunctional epoxy compound (B) per 100 parts by mass of the cycloolefin polymer (A) (i.e., the total of cycloolefin polymers (A-1) and (A-2)) in the presently disclosed radiation-sensitive resin composition is preferably 8 parts by mass or more, more preferably 15 parts by mass or more, and even more preferably 25 parts by mass or more, and is preferably 150 parts by mass or less, more preferably 100 parts by mass or less, and even more preferably 80 parts by mass or less. Extensibility of a resin film can be further improved when the content of the difunctional epoxy compound (B) is 8 parts by mass or more per 100 parts by mass of the cycloolefin polymer (A), whereas sufficient heat resistance of the resin film can be ensured and pattern loss by melting due to heat during patterning can be inhibited when the content of the difunctional epoxy compound (B) is 150 parts by mass or less per 100 parts by mass of the cycloolefin polymer (A).

The content of the difunctional epoxy compound (B) per 100 parts by mass of the cycloolefin polymer (A-2) in the presently disclosed radiation-sensitive resin composition is preferably 150 parts by mass or more, more preferably 170 parts by mass or more, even more preferably 200 parts by mass or more, and particularly preferably 225 parts by mass or more, and is preferably 750 parts by mass or less, more preferably 500 parts by mass or less, and even more preferably 350 parts by mass or less. When the content of the difunctional epoxy compound (B) is 150 parts by mass or more per 100 parts by mass of the cycloolefin polymer (A-2), a sufficient amount of the difunctional epoxy compound (B) can be ensured relative to the cycloolefin polymer (A-2) that has a comparatively high molecular weight and a large contribution to extensibility, and extensibility of a resin film can be even further improved. On the other hand, when the content of the difunctional epoxy compound (B) is 750 parts by mass or less per 100 parts by mass of the cycloolefin polymer (A-2), sufficient heat resistance of a resin film can be ensured, and pattern loss by melting due to heat during patterning can be inhibited.

<Radiation-Sensitive Compound (C)>

The radiation-sensitive compound (C) is a compound that can instigate a chemical reaction upon irradiation with activating radiation. Specifically, in a case in which an alkaline developer is used as a developer, it is preferable that a photoacid generator is used as the radiation-sensitive compound (C) so as to improve solubility of a photoexposed film in the alkaline developer. The radiation-sensitive compound (C) may be one type of compound used individually or two or more types of compounds used in combination.

<<Photoacid Generator>>

The photoacid generator may, for example, be an azide compound (for example, a quinone diazide compound), an onium salt compound, a halogenated organic compound, an α,α'-bis(sulfonyl)diazomethane compound, an α-carbonyl-α'-sulfonyldiazomethane compound, a sulfone compound, an organic acid ester compound, an organic acid amide compound, an organic acid imide compound, an acetophenone compound, a triarylsulfonium salt, or the like, is preferably an azide compound, and is more preferably a quinone diazide compound.

Examples of quinone diazide compounds that can suitably be used as the photoacid generator include an ester compound of a quinone diazide sulfonyl halide and a compound including a phenolic hydroxy group.

The quinone diazide sulfonyl halide used in preparation of the ester compound may, for example, be 1,2-naphthoquinone diazide-5-sulfonyl chloride, 1,2-naphthoquinone diazide-4-sulfonyl chloride, or 1,2-benzoquinone diazide-5-sulfonyl chloride.

The compound including a phenolic hydroxy group that is used in preparation of the ester compound may, for example, be 1,1,3-tris(2,5-dimethyl-4-hydroxyphenyl)-3-phenylpropane, 4,4'-[1-[4-[1-[4-hydroxyphenyl]-1-methylethyl]phenyl]ethylidene]bi sphenol, 2,3,4-trihydroxybenzophenone, 2,3,4,4'-tetrahydroxybenzophenone, 2-bis(4-hydroxyphenyl)propane, tris(4-hydroxyphenyl)methane, 1,1,1-tris(4-hydroxy-3-methylphenyl)ethane, 1,1,2,2-tetrakis(4-hydroxyphenyl)ethane, an oligomer of a novolac resin, or an oligomer obtained through copolymerization of a compound including at least one phenolic hydroxy group and dicyclopentadiene.

<<Content>>

The content of the radiation-sensitive compound (C) per 100 parts by mass of the cycloolefin polymer (A) (i.e., the total of cycloolefin polymers (A-1) and (A-2)) in the presently disclosed radiation-sensitive resin composition is preferably 10 parts by mass or more, more preferably 15 parts by mass or more, and even more preferably 25 parts by mass or more, and is preferably 100 parts by mass or less, more preferably 70 parts by mass or less, and even more preferably 50 parts by mass or less. When the content of the radiation-sensitive compound (C) is 10 parts by mass or more per 100 parts by mass of the cycloolefin polymer (A), solubility of the cycloolefin polymer (A) in developer in a photoexposed region can be sufficiently increased through irradiation with activating radiation, and development residue formation can be further inhibited. On the other hand, when the content of the radiation-sensitive compound (C) is 100 parts by mass or less per 100 parts by mass of the cycloolefin polymer (A), solubility of the cycloolefin polymer (A) in developer in a non-photoexposed region is not unintentionally increased, and a pattern shape having excellent resolution can be formed.

<Solvent>

The presently disclosed radiation-sensitive resin composition may contain a solvent. In other words, the presently disclosed radiation-sensitive resin composition may be a radiation-sensitive resin liquid in which the cycloolefin polymer (A-1), the cycloolefin polymer (A-2), the difunctional epoxy compound (B), the radiation-sensitive compound (C), and other optionally added compounding agents are dissolved and/or dispersed in a solvent.

The solvent may be any known solvent that is used as a solvent in resin compositions and examples thereof include linear ketones such as acetone, methyl ethyl ketone, cyclopentanone, 2-hexanone, 3-hexanone, 2-heptanone, 3-heptanone, 4-heptanone, 2-octanone, 3-octanone, and 4-octanone; alcohols such as n-propyl alcohol, isopropyl alcohol, n-butyl alcohol, and cyclohexanol; ethers such as ethylene glycol dimethyl ether, ethylene glycol diethyl ether, and dioxane; alcohol ethers such as ethylene glycol monomethyl ether and ethylene glycol monoethyl ether; esters such as propyl formate, butyl formate, propyl acetate, butyl acetate, methyl propionate, ethyl propionate, methyl butyrate, ethyl butyrate, methyl lactate, and ethyl lactate; cellosolve esters such as cellosolve acetate, methyl cellosolve acetate, ethyl cellosolve acetate, propyl cellosolve acetate, and butyl cellosolve acetate; propylene glycols such as propylene glycol, propylene glycol monomethyl ether, propylene glycol monomethyl ether acetate, propylene glycol monoethyl ether acetate, and propylene glycol monobutyl ether; diethylene glycols such as diethylene glycol monomethyl ether, diethylene glycol monoethyl ether, diethylene glycol dimethyl ether, diethylene glycol diethyl ether, and diethylene glycol methyl ethyl ether; saturated γ-lactones such as γ-butyrolactone, γ-valerolactone, γ-caprolactone, and γ-caprylolactone; halogenated hydrocarbons such as trichloroethylene; aromatic hydrocarbons such as toluene and xylene; and other polar solvents such as dimethylacetamide, dimethylformamide, and N-methylacetamide.

The solvent may be one type of solvent used individually or two or more types of solvents used in combination. The content of the solvent per 100 parts by mass of the cycloolefin polymer (A) (i.e., the total of cycloolefin polymers (A-1) and (A-2)) in the presently disclosed radiation-sensitive resin composition is preferably not less than 10 parts by mass and not more than 10,000 parts by mass, more preferably not less than 50 parts by mass and not more than 5,000 parts by mass, and even more preferably not less than 100 parts by mass and not more than 1,000 parts by mass.

<Other Compounding Agents>

The presently disclosed radiation-sensitive resin composition may contain compounding agents other than the components set forth above. Examples of such other compounding agents include crosslinking agents other than the difunctional epoxy compound (B) (other crosslinking agents), silane coupling agents, aralkyl phenolic resins, compounds including an acidic group or a thermally latent acidic group, surfactants, antioxidants, sensitizers, light stabilizers, defoamers, pigments, dyes, and fillers. Of these other compounding agents, it is preferable that the presently disclosed radiation-sensitive resin composition contains another crosslinking agent, a silane coupling agent, and an aralkyl phenolic resin. These other compounding agents may be one type used individually or two or more types used in combination.

<<Other Crosslinking Agents>>

Examples of crosslinking agents other than the difunctional epoxy compound (B) that may be used include epoxy group-containing crosslinking agents having a functionality of 3 or more (i.e., including three or more epoxy groups per molecule), oxetane group-containing crosslinking agents, isocyanate group-containing crosslinking agents, blocked isocyanate group-containing crosslinking agents, oxazoline group-containing crosslinking agents, maleimide group-containing crosslinking agents, (meth)acrylate group-containing crosslinking agents, compounds including at least two alkoxymethyl groups (alkoxymethyl group-containing crosslinking agents), and compounds including at least two methylol groups (methylol group-containing crosslinking agents). Of these other crosslinking agents, a compound including at least two alkoxymethyl groups and a compound including at least two methylol groups are preferable from a viewpoint of improving chemical resistance and low hygroscopicity of a resin film.

Note that in the present disclosure, "(meth)acrylate" is used to indicate "acrylate" and/or "methacrylate".

[Compound Including at Least Two Alkoxymethyl Groups]

The compound including at least two alkoxymethyl groups may, for example, be a phenolic compound in which at least two alkoxymethyl groups are directly bonded to an aromatic ring, a melamine compound in which amino groups are substituted with at least two alkoxymethyl groups, or a urea compound substituted with at least two alkoxymethyl groups.

Examples of phenolic compounds in which at least two alkoxymethyl groups are directly bonded to an aromatic ring include dimethoxymethyl-substituted phenolic compounds such as 2,6-dimethoxymethyl-4-t-butylphenol and 2,6-dimethoxymethyl-p-cresol; tetramethoxymethyl-substituted biphenyl compounds such as 3,3',5,5'-tetramethoxymethyl-4,4'-dihydroxybiphenyl (for example, TMOM-BP (product name) produced by Honshu Chemical Industry Co., Ltd.) and 1,1-bis[3,5-di(methoxymethyl)-4-hydroxyphenyl]-1-phenylethane; and hexamethoxymethyl-sub stituted triphenyl compounds such as 4,4',4"-(ethylidene)trisphenol (for example, HMOM-TPHAP-GB (product name) produced by Honshu Chemical Industry Co., Ltd.).

Examples of melamine compounds in which amino groups are substituted with at least two alkoxymethyl groups include N,N'-dimethoxymethylmelamine, N,N',N"-trimethoxymethylmelamine, N,N,N',N"-tetramethoxymethylmelamine, N,N,N',N',N"-pentamethoxymethylmelamine, N,N,N',N',N",N"-hexamethoxymethylmelamine (for example, NIKALAC MW-390LM (product name) and NIKALAC MW-100LM (product name) produced by Sanwa Chemical Co., Ltd.), and polymers thereof.

Examples of urea compounds substituted with at least two alkoxymethyl groups include NIKALAC MX270 (product name), NIKALAC MX280 (product name), and NIKALAC MX290 (product name) produced by Sanwa Chemical Co., Ltd.

[Compound Including at Least Two Methylol Groups]

The compound including at least two methylol groups may, for example, be a phenolic compound in which at least two methylol groups are directly bonded to an aromatic ring.

Examples of phenolic compounds in which at least two methylol groups are directly bonded to an aromatic ring include 2,4-2,4-dihydroxymethyl-6-methylphenol, 2,6-bis(hydroxymethyl)-p-cresol, 4-tert-2,6-bis(hydroxymethyl)phenol, bis(2-hydroxy-3-hydroxymethyl-5-methylphenyl)methane (DM-BIPC-F (product name) produced by Asahi Yukizai Corporation), bis(4-hydroxy-3-hydroxymethyl-5-methylphenyl)methane (DM-BIOC-F (product name) produced by Asahi Yukizai Corporation), and 2,2-bis(4-hydroxy-3,5-dihydroxymethylphenyl)propane (TM-BIP-A (product name) produced by Asahi Yukizai Corporation).

Of the compounds including at least two alkoxymethyl groups and the compounds including at least two methylol groups described above, N,N,N',N',N",N"-hexamethoxymethylmelamine is preferable in terms of having high reactivity.

[Content]

The content of crosslinking agents other than the difunctional epoxy compound (B) per 100 parts by mass of the cycloolefin polymer (A) (i.e., the total of cycloolefin polymers (A-1) and (A-2)) in the presently disclosed radiation-sensitive resin composition is preferably not less than 1 part by mass and not more than 80 parts by mass, more preferably not less than 5 parts by mass and not more than 75 parts by mass, and even more preferably not less than 10 parts by mass and not more than 70 parts by mass. When the content of crosslinking agents other than the difunctional epoxy compound (B) is within any of the ranges set forth above, low hygroscopicity and chemical resistance of a resin film can be improved.

<<Silane Coupling Agent>>

Compounding of a silane coupling agent in the presently disclosed radiation-sensitive resin composition can improve close adherence of a resin film to metal. Examples of silane coupling agents that may be used include, but are not specifically limited to, silane compounds including a reactive functional group such as an amino group, a carboxyl group, a methacryloyl group, an isocyanate group, or an epoxy group.

Specific examples of silane coupling agents that may be used include β-aminopropyltrimethoxysilane, 3-aminopropyltriethoxysilane, N-2-(aminoethyl)-3-aminopropyltrimethoxysilane, N-phenyl-3-aminopropyltrimethoxysilane, trimethoxysilylbenzoic acid, γ-methacryloxypropyltrimethoxysilane, γ-methacryloxypropyltriethoxysilane, γ-isocyanatopropyltrimethoxysilane, γ-isocyanatopropyltriethoxysilane, γ-glycidoxypropyltrimethoxysilane, γ-glycidoxypropyltriethoxysilane, β-(3,4-epoxycyclohexyl)ethyltrimethoxysilane, and β-(3,4-epoxycyclohexyl)ethyltriethoxysilane. Of these silane coupling agents, γ-glycidoxypropyltrim ethoxysil ane and N-phenyl-3-aminopropyltrimethoxysilane are preferable, and N-phenyl-3-aminopropyltrimethoxysilane and γ-glycidoxypropyltrimethoxysilane are more preferable.

[Content]

The content of the silane coupling agent per 100 parts by mass of the cycloolefin polymer (A) (i.e., the total of cycloolefin polymers (A-1) and (A-2)) in the presently disclosed radiation-sensitive resin composition is preferably not less than 0.01 parts by mass and not more than 100 parts by mass, more preferably not less than 0.1 parts by mass and not more than 50 parts by mass, and even more preferably not less than 0.5 parts by mass and not more than 20 parts by mass. Close adherence of a resin film to metal can be further improved by setting the content of the silane coupling agent within any of the ranges set forth above.

<<Aralkyl Phenolic Resin>>

Compounding of an aralkyl phenolic resin in the presently disclosed radiation-sensitive resin composition can improve close adherence of a resin film to metal. The aralkyl phenolic resin is not specifically limited and may, for example, be an aralkyl phenolic resin such as described in WO 2015/141717 A1.

The content of the aralkyl phenolic resin per 100 parts by mass of the cycloolefin polymer (A) (i.e., the total of cycloolefin polymers (A-1) and (A-2)) in the presently disclosed radiation-sensitive resin composition is preferably not less than 5 parts by mass and not more than 50 parts by mass, more preferably not less than 10 parts by mass and not more than 45 parts by mass, and even more preferably not less than 15 parts by mass and not more than 35 parts by mass. Close adherence of a resin film to metal can be further improved by setting the content of the aralkyl phenolic resin within any of the ranges set forth above.

<Preparation Method of Radiation-Sensitive Resin Composition>

No specific limitations are placed on how the presently disclosed radiation-sensitive resin composition is prepared. For example, the presently disclosed radiation-sensitive resin composition may be prepared by mixing the various components forming the radiation-sensitive resin composition.

Specifically, the presently disclosed radiation-sensitive resin composition is preferably obtained by mixing the above-described cycloolefin polymer (A-1) including a protonic polar group, cycloolefin polymer (A-2) including a protonic polar group, difunctional epoxy compound (B), radiation-sensitive compound (C), and other optionally used compounding agents in the above-described solvent in order to dissolve or disperse these components in the solvent. Through this operation, the radiation-sensitive resin composition is obtained in the form of a solution or dispersion liquid (i.e., a radiation-sensitive resin liquid).

The mixing can be performed using a known mixer without any specific limitations. Moreover, filtration may be performed by a known method after the mixing.

The solid content concentration of the radiation-sensitive resin liquid (presently disclosed radiation-sensitive resin composition) is normally not less than 1 mass % and not more than 70 mass %, preferably not less than 5 mass % and not more than 60 mass %, and more preferably not less than 10 mass % and not more than 50 mass %. When the solid content concentration is within any of the ranges set forth above, it is possible to obtain a balance of high levels of dissolution stability and coatability of the radiation-sensitive resin liquid and thickness uniformity and flatness of a formed resin film.

(Electronic Component)

The presently disclosed electronic component includes a resin film formed from the presently disclosed radiation-sensitive resin composition set forth above. The presently disclosed electronic component has high performance as a result of including a resin film that is formed from the presently disclosed radiation-sensitive resin composition and that has sufficiently little development residue and excellent extensibility.

<Type of Electronic Component>

The presently disclosed electronic component is suitable as an electronic component produced by wafer level packaging technology because the resin film formed from the presently disclosed radiation-sensitive resin composition has sufficiently little development residue and excellent extensibility, but is not specifically limited thereto. In particular, the resin film formed from the presently disclosed radiation-sensitive resin composition is particularly suitable as a resin film that forms an interlayer insulating film for insulating between wiring disposed in a layer-like form (for example, an interlayer insulating film for rewiring) in an electronic component produced by wafer level packaging technology.

<Formation of Resin Film>

No specific limitations are placed on how the electronic component including the resin film is produced. For example, the electronic component including the resin film may be produced by forming a resin film on a substrate such as a silicon wafer populated with semiconductor elements, and then the substrate on which the resin film has been formed may be used as an electronic component or may be incorporated into an electronic component.

Also, no specific limitations are placed on how the resin film is formed on the substrate. For example, the resin film may be produced through a step of using a radiation-sensitive resin composition containing a solvent (i.e., a radiation-sensitive resin liquid) to form a radiation-sensitive film on a substrate (radiation-sensitive film formation step), a step of irradiating the radiation-sensitive film with activating radiation to obtain a photoexposed film (photoexposure step), a step of developing the photoexposed film to obtain a developed film (development step), and a step of crosslinking the developed film to obtain a resin film (crosslinking step).

<<Radiation-Sensitive Film Formation Step>>

The method by which the radiation-sensitive film is formed on the substrate using the radiation-sensitive resin liquid is not specifically limited and may, for example, be a method such as an application method or a film lamination method.

[Application Method]

The application method is a method in which the radiation-sensitive resin liquid is applied onto the substrate and then the solvent is removed by heated drying to form the radiation-sensitive film. Various methods such as spraying, spin coating, roll coating, die coating, doctor blading, rotary coating, slit coating, bar coating, screen printing, and inkjet printing may be adopted as the method by which the radiation-sensitive resin liquid is applied. The heated drying conditions differ depending on the types and proportions of components. However, the heating temperature is normally 30° C. to 150° C., and preferably 60° C. to 130° C., whereas the heating time is normally 0.5 minutes to 90 minutes, preferably 1 minute to 60 minutes, and more preferably 1 minute to 30 minutes.

[Film Lamination Method]

The film lamination method is a method in which the radiation-sensitive resin liquid is applied onto a base material for radiation-sensitive film formation (for example, a resin film or a metal film), the solvent is subsequently removed by heated drying to obtain a radiation-sensitive film, and then the obtained radiation-sensitive film is laminated on the substrate. The heated drying conditions can be selected as appropriate depending on the types and proportion of components, but the heating temperature is normally 30° C. to 150° C. and the heating time is normally 0.5 minutes to 90 minutes. Lamination of the radiation-sensitive film on the substrate may be performed using a pressure bonding machine such as a press laminator, a press, a vacuum laminator, a vacuum press, or a roll laminator.

The thickness of the radiation-sensitive film that is formed on the substrate by any of the methods described above is not specifically limited and may be set as appropriate depending on the intended use, but is preferably 0.1 μm to 100 μm, more preferably 0.5 μm to 50 μm, and even more preferably 0.5 μm to 30 μm.

<<Photoexposure Step>>

Next, the radiation-sensitive film that has been formed in the radiation-sensitive film formation step described above is irradiated with activating radiation to obtain a photoexposed film having a latent image pattern.

[Activating Radiation]

No specific limitations are placed on the activating radiation other than being radiation that can activate the radiation-sensitive compound (C) contained in the radiation-sensitive film and thereby improve solubility of the cycloolefin polymer (A) in developer (particularly solubility in alkaline developer) in a photoexposed region. Specific examples of activating radiation that may be used include light such as ultraviolet light (inclusive of ultraviolet light of a single wavelength such as g-line or i-line ultraviolet light), KrF excimer laser light, and ArF excimer laser light; and particle beams such as an electron beam.

In a case in which light is used as the activating radiation, the light may be single-wavelength light or mixed-wavelength light.

[Photoexposure Conditions]

Formation of a latent image pattern through selective irradiation with the activating radiation in the form of a pattern can be performed by a standard method. For example, it is possible to adopt a method in which a stepper or the like is used to perform irradiation with light (for example, ultraviolet light, KrF excimer laser light, or ArF excimer laser light) through a desired mask pattern or a method in which writing is performed using a particle beam such as an electron beam.

The irradiation conditions can be selected as appropriate depending on the activating radiation that is used. For example, in a case in which light having a wavelength of 200 nm to 450 nm is used, the irradiation dose is normally 10 mJ/cm$^2$ to 5,000 mJ/cm$^2$, and preferably 50 mJ/cm$^2$ to 1,500 mJ/cm$^2$, and is determined by the irradiation time and the illuminance. After the irradiation with activating radiation, the resultant photoexposed film may be subjected to heat treatment at a temperature of approximately 60° C. to 150° C. for approximately 1 minute to 10 minutes as necessary.

<<Development Step>>

Next, the latent image pattern formed in the photoexposed film in the photoexposure step described above is developed using a developer so as to reveal the pattern and obtain a developed film.

[Developer]

The developer may be an alkaline developer. The alkaline developer can be obtained by dissolving an alkaline compound in an aqueous medium.

The alkaline compound may, for example, be an alkali metal salt, an amine, or an ammonium salt. Moreover, the alkaline compound may be an inorganic compound or an organic compound. Specific examples of alkaline compounds that may be used include alkali metal salts such as sodium hydroxide, potassium hydroxide, sodium carbonate, sodium silicate, and sodium metasilicate; ammonia; primary amines such as ethylamine and n-propylamine; secondary amines such as diethylamine and di-n-propylamine; tertiary amines such as triethylamine and methyldiethylamine; quaternary ammonium salts such as tetramethylammonium hydroxide, tetraethylammonium hydroxide, tetrabutylammonium hydroxide, and choline; alcohol amines such as dimethylethanolamine and triethanolamine; and cyclic amines such as pyrrole, piperidine, 1,8-diazabicyclo[5.4.0]undec-7-ene, 1,5-diazabicyclo[4.3.0]non-5-ene, and N-methylpyrrolidone. One of these alkaline compounds may be used individually, or two or more of these alkaline compounds may be used in combination.

The aqueous medium of the alkaline developer may be water or a water-soluble organic solvent such as methanol or ethanol.

Moreover, an appropriate amount of a surfactant or the like may be added to the alkaline developer.

[Development Method]

The method by which the developer is brought into contact with the photoexposed film having a latent image pattern may, for example, be a method such as a paddle method, a spray method, or a dipping method. The development temperature can be selected as appropriate from a range of normally 0° C. to 100° C., preferably 5° C. to 55° C., and more preferably 10° C. to 30° C., and the development time can be selected as appropriate from a range of normally 30 seconds to 180 seconds.

The developed film having a target pattern formed therein in this manner may be rinsed using a rinsing liquid as necessary in order to remove development residue. Rinsing liquid remaining after rinsing is preferably removed using compressed air or compressed nitrogen.

Moreover, the developed film may be irradiated with activating radiation as necessary in order to deactivate radiation-sensitive compound (C) remaining in the developed film. The irradiation with activating radiation may be performed using any of the methods previously described in the "Photoexposure step" section. Also note that the developed film may be heated concurrently to irradiation with activating radiation or after irradiation with activating radiation. The method of heating may, for example, be a method of heating the electronic component on a hot plate or inside an oven. The heating temperature is normally 80° C. to 300° C., and preferably 100° C. to 200° C.

<<Crosslinking Step>>

The developed film that has been patterned in the development step described above is crosslinked to obtain a patterned resin film.

The method of crosslinking may be selected as appropriate depending on the type of crosslinking agent (difunctional epoxy compound (B), etc.) contained in the radiation-sensitive resin liquid, but is normally performed by heating.

The method of heating may involve using a hot plate, an oven, or the like, for example. The heating temperature is normally 150° C. to 250° C. and the heating time may be selected as appropriate depending on the area and thickness of the developed film, the device used for heating, and so forth. For example, the heating time is normally 5 minutes to 120 minutes in a case in which a hot plate is used and is normally 30 minutes to 150 minutes in a case in which an oven is used. The heating may be performed in an inert gas atmosphere as necessary. The inert gas may be a gas that does not include oxygen and does not cause oxidation of the developed film. Examples of the inert gas include nitrogen, argon, helium, neon, xenon, and krypton. Of these inert gases, nitrogen and argon are preferable, and nitrogen is particularly preferable. In particular, an inert gas (particularly nitrogen) having an oxygen content of 0.1 volume % or less, and preferably 0.01 volume % or less is suitable. One of these inert gases may be used individually, or two or more of these inert gases may be used in combination.

EXAMPLES

The following provides a more specific description of the present disclosure based on examples. However, the present disclosure is not limited to the following examples.

In the examples and comparative examples, the tensile elongation, tensile elastic modulus, and inhibition of development residue formation were evaluated as follows.

<Tensile Elongation and Tensile Elastic Modulus>

A radiation-sensitive resin liquid prepared in each example or comparative example was spin coated onto a silicon wafer on which an aluminum thin film of 100 nm in thickness had been formed using a sputtering apparatus, and then the radiation-sensitive resin liquid was heated at 120° C. for 2 minutes using a hot plate. Next, curing was performed in a nitrogen atmosphere at 180° C. for 60 minutes to obtain a laminate including a cured film of 10 μm in thickness at one side thereof.

The obtained laminate was immersed in 0.5 mol/L hydrochloric acid aqueous solution so that the aluminum thin film positioned between the silicon wafer and the cured film dissolved in the hydrochloric acid aqueous solution to thereby enable peeling of the cured film from the silicon wafer. The cured film that had been peeled off was subsequently washed with water and dried. A specimen of 5 mm×50 mm was cut out from the post-drying cured film. This specimen was subjected to a tensile test to measure the tensile elongation and tensile elastic modulus. Specifically, the tensile elongation (%) and tensile elastic modulus (GPa) of the specimen were measured by using an AUTOGRAPH (AGS-5kNG produced by Shimadzu Corporation) to perform a tensile test under conditions of a chuck separation of 20 mm, a tensile rate of 2 mm/min, and a measurement temperature of 23° C. Five specimens were cut out from the cured film and average values of values measured for the specimens were evaluated by the following standards. It is preferable that the cured film formed from the radiation-sensitive resin liquid has a high tensile elongation because this means that a resin film formed from the radiation-sensitive resin liquid is less susceptible to cracking and peeling during a high-temperature cycle test or a drop impact test. Moreover, it is preferable that the cured film formed from the radiation-sensitive resin liquid has a low tensile elastic modulus because this means that warping of a substrate including a resin film formed from the radiation-sensitive resin liquid is inhibited.

[Tensile Elongation]
A: Tensile elongation of 20% or more
B: Tensile elongation of not less than 10% and less than 20%
C: Tensile elongation of less than 10%

[Tensile Elastic Modulus]
A: Tensile elastic modulus of less than 2 GPa
B: Tensile elastic modulus of not less than 2 GPa and less than 2.2 GPa
C: Tensile elastic modulus of 2.2 GPa or more <Inhibition of Development Residue Formation>

A radiation-sensitive resin liquid prepared in each example or comparative example was spin coated onto a silicon wafer and was prebaked at 120° C. for 2 minutes using a hot plate to form a radiation-sensitive film of μm in thickness. Next, a high-pressure mercury lamp emitting light of the g-line (436 nm), h-line (405 nm), and i-line (365 nm) wavelengths was used to perform photoexposure at 400 mJ/cm$^2$. The photoexposed film was developed by immersion in 2.38% tetramethylammonium hydroxide aqueous solution (alkaline developer) at 23° C. for 3 minutes, and was subsequently rinsed with ultrapure water for 30 seconds. The condition of the photoexposed film was inspected by eye and was evaluated by the following standard. A case in which non-dissolution and swelling do not occur is preferable because this means that development residue formation is effectively inhibited.

A: Photoexposed film is completely dissolved
B: Photoexposed film is partially dissolved but part remains undissolved or swollen
C: Entire photoexposed film remains undissolved or swollen Example 1

<Preparation of Cycloolefin Polymer (A-1)>

A glass pressure-resistant reactor that had been purged with nitrogen was charged with 100 parts by mass of a monomer mixture comprising 40 mol % of N-phenyl-bicyclo[2.2.1]hept-5-ene-2,3-dicarboxyimide (NBPI) and 60 mol % of 4-hydroxycarbonyltetracyclo[6.2.1.1$^{3,6}$.0$^{2,7}$]dodec-9-ene (TCDC), 2.0 parts by mass of 1,5-hexadiene, 0.02 parts by mass of (1,3-dimesitylimidazolin-2-ylidene)(tricyclohexylphosphine)benzylideneruthenium dichloride (synthesized by method described in "Org. Lett., Vol. 1, p. 953, 1999"), and 200 parts by mass of diethylene glycol ethyl methyl ether. These materials were reacted under stirring at 80° C. for 4 hours to obtain a polymerization reaction liquid.

The obtained polymerization reaction liquid was loaded into an autoclave and was subjected to a hydrogenation reaction under stirring at 150° C. and a hydrogen pressure of 4 MPa for 5 hours to obtain a polymer solution containing a cycloolefin polymer (A-1). The obtained cycloolefin polymer (A-1) had a polymerization conversion rate of 99.7 mass %, a polystyrene-equivalent weight-average molecular weight of 7,150, a number-average molecular weight of 4,690, a molecular weight distribution of 1.52, and a percentage hydrogenation of 99.7 mol %. The solid content concentration of the obtained polymer solution of the cycloolefin polymer (A-1) was 34.4 mass %.

<Preparation of Cycloolefin Polymer (A-2)>

A glass pressure-resistant reactor that had been purged with nitrogen was charged with 100 parts by mass of a monomer mixture comprising 16 mol % of N-phenyl-bicyclo[2.2.1]hept-5-ene-2,3-dicarboxyimide (NBPI), 16 mol % of N-(2-ethylhexyl)-bicyclo[2.2.1]hept-5-ene-2,3-dicarboxyimide (NEHI), and 68 mol % of 4-hydroxycarbonyltetracyclo[6.2.1.1$^{3,6}$.0$^{2,7}$]dodec-9-ene (TCDC), 1.0 parts by mass of 1-hexene, 0.06 parts by mass of (1,3-dimesitylimidazolin-2-ylidene)(tricyclohexylphosphine)benzylideneruthenium dichloride (synthesized by method described in "Org. Lett., Vol. 1, p. 953, 1999"), and 300 parts by mass of diethylene glycol ethyl methyl ether. These materials were reacted under stirring at 80° C. for 4 hours to obtain a polymerization reaction liquid.

The obtained polymerization reaction liquid was loaded into an autoclave and was subjected to a hydrogenation reaction under stirring at 150° C. and a hydrogen pressure of 4 MPa for 5 hours to obtain a polymer solution containing a cycloolefin polymer (A-2). The obtained cycloolefin polymer (A-2) had a polymerization conversion rate of 99.3 mass %, a polystyrene-equivalent weight-average molecular weight of 20,600, a number-average molecular weight of 11,500, a molecular weight distribution of 1.79, and a percentage hydrogenation of 99.8 mol %. The solid content concentration of the obtained polymer solution of the cycloolefin polymer (A-2) was 25.3 mass %.

<Preparation of Radiation-Sensitive Resin Liquid>

A radiation-sensitive resin liquid was prepared as a radiation-sensitive resin composition by mixing 90 parts in terms of solid content of the polymer solution of the cycloolefin polymer (A-1) and 10 parts in terms of solid content of the polymer solution of the cycloolefin polymer (A-2) as a cycloolefin polymer (A), 45 parts of a difunctional linear epoxy compound (jER YX7400 (product name) produced by Mitsubishi Chemical Corporation; epoxy equivalent: 440; softening point: 25° C. or lower (liquid at normal temperature); compound for which $R^1$ is —$C_4H_8$— and k is approximately 10 in formula (1)) as a difunctional epoxy compound (B), 40 parts of a condensate of 4,4'-[1-[4-[1-[4-hydroxyphenyl]-1-methylethyl]phenyl]ethylidene]bi sphenol (1.0 molar parts) and 1,2-naphthoquinone diazide-5-sulfonyl chloride (2.0 molar parts) (TS200 (product name) produced by Toyo Gosei Co., Ltd.; quinone diazide compound) as a radiation-sensitive compound (C), 7.5 parts of a tetrafunctional alicyclic epoxy resin (Epolead GT401 (product name) produced by Daicel Corporation; ε-caprolactone modified tetra(3,4-epoxycyclohexylmethyl) butanetetracarboxylate) and 10 parts of a compound including at least two alkoxymethyl groups (product name: NIKALAC MW-100LM; N,N,N',N',N'',N''-hexamethoxymethylmelamine) as other crosslinking agents, 25 parts of an aralkyl phenolic resin (KAYAHARD GPH-65 (product name) produced by Nippon Kayaku Co., Ltd.; softening point: 65° C.; hydroxy group equivalent: 198 g/eq) as a curing agent, 1 part of N-phenyl-3-aminopropyltrimethoxysilane (KBM-573 (product name) produced by Shin-Etsu Silicone) and 4 parts of γ-glycidoxypropyltrimethoxysilane (Z6040 (product name) produced by Dow Corning Toray Co., Ltd.) as silane coupling agents, and 160 parts of diethylene glycol ethyl methyl ether as a solvent, and subsequently filtering the resultant mixture using a polytetrafluoroethylene filter having a pore diameter of 0.45 μm. The obtained radiation-sensitive resin liquid was used to perform each of the evaluations. The results are shown in Table 1.

Examples 2 to 4

A radiation-sensitive resin liquid was prepared as a radiation-sensitive resin composition in the same way as in Example 1 with the exception that the amounts of the cycloolefin polymer (A-1) and the cycloolefin polymer (A-2) were changed as shown in Table 1. The obtained radiation-sensitive resin liquid was used to perform each of the evaluations. The results are shown in Table 1.

Comparative Examples 1 to 3

A radiation-sensitive resin liquid was prepared as a radiation-sensitive resin composition in the same way as in Example 1 with the exception that the amounts of the cycloolefin polymer (A-1) and the cycloolefin polymer (A-2) were changed as shown in Table 1. The obtained radiation-sensitive resin liquid was used to perform each of the evaluations. The results are shown in Table 1.

Comparative Example 4

A radiation-sensitive resin liquid was prepared as a radiation-sensitive resin composition in the same way as in Example 1 with the exception that the amounts of the cycloolefin polymer (A-1) and the cycloolefin polymer (A-2) were changed as shown in Table 1, and the amounts of the difunctional linear epoxy compound and the tetrafunctional alicyclic epoxy resin were changed as shown in Table 1. The obtained radiation-sensitive resin liquid was used to perform each of the evaluations. The results are shown in Table 1.

TABLE 1

| | | | Example 1 | Example 2 | Example 3 | Example 4 |
|---|---|---|---|---|---|---|
| Radiation-sensitive resin composition | | Cycloolefin polymer (A-1) [parts by mass] | 90 | 80 | 85 | 60 |
| | | Cycloolefin polymer (A-2) [parts by mass] | 10 | 20 | 15 | 40 |
| | Difunctional epoxy compound (B) | Difunctional linear epoxy compound [parts by mass] | 45 | 45 | 45 | 45 |
| | Radiation-sensitive compound (C) | Quinone diazide compound [parts by mass] | 40 | 40 | 40 | 40 |
| | Other compounding agents | Other crosslinking agents | Tetrafunctional alicyclic epoxy resin [parts by mass] | 7.5 | 7.5 | 7.5 | 7.5 |
| | | | Compound including at least two alkoxymethyl groups [parts by mass] | 10 | 10 | 10 | 10 |
| | | Aralkyl phenolic resin [parts by mass] | 25 | 25 | 25 | 25 |
| | | Silane coupling agent | N-Phenyl-3-aminopropyltrimethoxysilane [parts by mass] | 1 | 1 | 1 | 1 |
| | | | γ-Glycidoxypropyltrimethoxysilane [parts by mass] | 4 | 4 | 4 | 4 |
| | Amount of difunctional epoxy compound (B) per 100 parts by mass of cycloolefin polymer (A-2) [parts by mass] | | 450 | 225 | 300 | 112.5 |
| Evaluation | | Tensile elongation | B | A | A | B |
| | | Tensile elastic modulus | A | A | A | A |
| | | Inhibition of development residue formation | A | A | A | B |

| | | | Comparative Example 1 | Comparative Example 2 | Comparative Example 3 | Comparative Example 4 |
|---|---|---|---|---|---|---|
| Radiation-sensitive resin composition | | Cycloolefin polymer (A-1) [parts by mass] | 100 | 40 | — | — |
| | | Cycloolefin polymer (A-2) [parts by mass] | — | 60 | 100 | 100 |
| | Difunctional epoxy compound (B) | Difunctional linear epoxy compound [parts by mass] | 45 | 45 | 45 | 70 |
| | Radiation-sensitive compound (C) | Quinone diazide compound [parts by mass] | 40 | 40 | 40 | 40 |
| | Other compounding | Other crosslinking | Tetrafunctional alicyclic epoxy resin [parts by mass] | 7.5 | 7.5 | 7.5 | 5 |

TABLE 1-continued

| | | | | | | |
|---|---|---|---|---|---|---|
| | agents | agents | Compound including at least two alkoxymethyl groups [parts by mass] | 10 | 10 | 10 | 10 |
| | | | Aralkyl phenolic resin [parts by mass] | 25 | 25 | 25 | 25 |
| | | Silane coupling agent | N-Phenyl-3-aminopropyltrimethoxysilane [parts by mass] | 1 | 1 | 1 | 1 |
| | | | γ-Glycidoxypropyltrimethoxysilane [parts by mass] | 4 | 4 | 4 | 4 |
| | Amount of difunctional epoxy compound (B) per 100 parts by mass of cycloolefin polymer (A-2) [parts by mass] | | | — | 75 | 45 | 70 |
| Evaluation | Tensile elongation | | | C | C | B | A |
| | Tensile elastic modulus | | | A | A | A | A |
| | Inhibition of development residue formation | | | A | C | C | C |

It can be seen from Table 1 that development residue formation can be sufficiently inhibited and a resin film having excellent extensibility can be formed using the radiation-sensitive resin compositions of Examples 1 to 4, which each contain a cycloolefin polymer (A-1) and a cycloolefin polymer (A-2) in a specific quantitative ratio as a cycloolefin polymer (A), a difunctional epoxy compound (B), and a radiation-sensitive compound (C). It can also be seen that a substrate with an attached resin film that is resistant to warping can be formed using the radiation-sensitive resin compositions of Examples 1 to 4.

On the other hand, it can be seen that excellent extensibility of a resin film cannot be ensured with the radiation-sensitive resin composition of Comparative Example 1 in which a cycloolefin polymer (A-1) having a low molecular weight is used alone as a cycloolefin polymer (A).

Moreover, it can be seen that excellent extensibility of a resin film cannot be ensured and development residue formation cannot be sufficiently inhibited with the radiation-sensitive resin composition of Comparative Example 2, which contains a small amount of a cycloolefin polymer (A-1) having a low molecular weight and a large amount of a cycloolefin polymer (A-2) having a high molecular weight compared to Examples 1 to 4.

Furthermore, it can be seen that development residue formation cannot be sufficiently inhibited with the radiation-sensitive resin composition of Comparative Example 3 in which a cycloolefin polymer (A-2) having a high molecular weight is used alone as a cycloolefin polymer (A).

In the case of the radiation-sensitive resin composition of Comparative Example 4 in which a cycloolefin polymer (A-2) having a high molecular weight is used alone as a cycloolefin polymer (A) and in which the amount of a difunctional epoxy compound (B) is increased compared to Examples 1 to 4, it can be seen that extensibility of a resin film can be ensured to a certain extent through the increased amount of the difunctional epoxy compound (B). However, it can also be seen that development residue formation of a resin film cannot be sufficiently inhibited using the radiation-sensitive resin composition of Comparative Example 4.

INDUSTRIAL APPLICABILITY

According to the present disclosure, it is possible to provide a radiation-sensitive resin composition capable of forming a resin film for which development residue formation is sufficiently inhibited and that has excellent extensibility.

Moreover, according to the present disclosure, it is possible to provide an electronic component having high performance.

The invention claimed is:

1. A radiation-sensitive resin composition comprising:
a cycloolefin polymer (A-1) including a protonic polar group;
a cycloolefin polymer (A-2) including a protonic polar group;
a difunctional epoxy compound (B); and
a radiation-sensitive compound (C), wherein
the cycloolefin polymer (A-1) has a weight-average molecular weight of not less than 1,000 and less than 10,000, and the cycloolefin polymer (A-2) has a weight-average molecular weight of not less than 10,000 and not more than 100,000, and
content of the cycloolefin polymer (A-2) is not less than 5 mass% and not more than 55 mass% of total content of the cycloolefin polymer (A-1) and the cycloolefin polymer (A-2).

2. The radiation-sensitive resin composition according to claim 1, wherein the difunctional epoxy compound (B) is represented by formula (1), shown below,

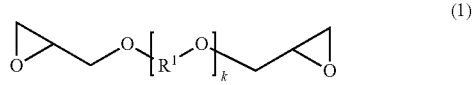

(1)

where, in formula (1), $R^1$ is a linear alkylene group having a carbon number of not less than 1 and not more than 15 or a branched alkylene group having a carbon number of not less than 3 and not more than 15, and k is an integer of not less than 1 and not more than 20.

3. The radiation-sensitive resin composition according to claim 1, wherein content of the difunctional epoxy compound (B) is 150 parts by mass or more per 100 parts by mass of the cycloolefin polymer (A-2).

4. The radiation-sensitive resin composition according to claim 1, further comprising a compound including at least two alkoxymethyl groups and/or a compound including at least two methylol groups.

5. The radiation-sensitive resin composition according to claim 1, further comprising a silane coupling agent.

6. The radiation-sensitive resin composition according to claim 1, further comprising an aralkyl phenolic resin.

7. An electronic component having a resin film comprising the radiation-sensitive resin composition according to claim 1.

* * * * *